(12) United States Patent
Matsuzawa et al.

(10) Patent No.: US 7,585,623 B2
(45) Date of Patent: Sep. 8, 2009

(54) ADIPONECTIN PROMOTER AND USE THEREOF

(75) Inventors: Yuji Matsuzawa, Takarazuka (JP); Iichiro Shimomura, 33-11, Higashitoyonakamachi 1-chome, Toyonaka-shi, Osaka (JP) 560-0003; Makoto Makishima, Nerima-ku (JP); Tohru Funahashi, Suita (JP); Masanori Iwaki, Mishima-gun (JP)

(73) Assignees: Ono Pharmaceutical Co., Ltd., Osaka (JP); Iichiro Shimomura, Osaka (JP)

( * ) Notice: Subject to any disclaimer, the term of this patent is extended or adjusted under 35 U.S.C. 154(b) by 62 days.

(21) Appl. No.: 10/540,864

(22) PCT Filed: Dec. 25, 2003

(86) PCT No.: PCT/JP03/16772
§ 371 (c)(1),
(2), (4) Date: Jun. 27, 2005

(87) PCT Pub. No.: WO2004/058970
PCT Pub. Date: Jul. 15, 2004

(65) Prior Publication Data
US 2006/0084618 A1 Apr. 20, 2006

(30) Foreign Application Priority Data
Dec. 26, 2002 (JP) ............................. 2002-376589

(51) Int. Cl.
*C12Q 1/68* (2006.01)
*C12N 15/63* (2006.01)
(52) U.S. Cl. .......................... 435/6; 435/455
(58) Field of Classification Search ....................... None
See application file for complete search history.

(56) References Cited
FOREIGN PATENT DOCUMENTS
WO WO 00/26363 A1 5/2000
WO WO 02/083726 A2 10/2002

OTHER PUBLICATIONS

Schaffler et al. (1998) 187-197.*
Entrez Nucleotide Sequence Database entry for AJ011119.*
Entrez Nucleotide Sequence Database entry for AF304467.*
Diez et al. (2003) Eur. J. Endocrinol. 148:293-300.*
Wagner (2002) Dis. Markers 18:41-46.*
Frank et al. (2003) Nature Rev. 2:566-580.*
Feng et al. (2004) Pharmacogenomics 5:709-719.*
Iwaki et al. (2003) Diabetes 52:1655-1663.*
Schaffler et al. (1998) 187-197.*
Entrez Nucleotide Sequence Database entry for AJ011119 (2007).*
Entrez Nucleotide Sequence Database entry for AF304467 (2007).*
Kallol Das, et al., "Chromosomal Localization, Expression Pattern, and Promoter Analysis of the Mouse Gene Encoding Adipocyte-Specific Secretory Protein Acrp30", Biochemical and Biophysical Research Communications, 2001, pp. 1120-1129, vol. 280, No.4.
International Search Report dated Mar. 9, 2004.
XP-002356642 (2000) *"Homo sapiens* adipocyte complement-related protein (ACRP30) gene, promoter region and 5' flanking sequence", Database EMBL (2 pages).
XP-002356628, M. Takahashi et al. (2000), "Genomic structure and mutations in adipose-specific gene, adiponectin", International Journal of Obesity, vol. 24, No. 7, pp. 861-868.
XP-002242792, T. Yamauchi et al. (2001), "The fat-derived hormone adiponectin reverses insulin resistance associated with both lipoatrophy and obesity", Nature Medicine, Nature Publishing Group, New York, vol. 7, No. 8, pp. 941-946.
Partial European Search Report dated Dec. 20, 2005.

* cited by examiner

*Primary Examiner*—Michael Burkhart
(74) *Attorney, Agent, or Firm*—Sughrue Mion, PLLC

(57) ABSTRACT

The present invention relates to a DNA having a promoter region containing regulatory sequences of human adiponectin gene, transformants transformed with the DNA, a screening method of a compound which can enhance the human adiponectin promoter activity, which the transformants are used, and the screening kit, and a screening method of a preventive/therapeutic medicine for syndromes such as Syndrome X, metabolic syndrome, multiple risk factor syndrome, insulin resistant syndrome, deadly quartet, and visceral fat syndrome, metabolic disorders such as diabetes, obesity, hypercholesterolemia, and hyperlipoproteinemias, hyperlipidemia, arteriosclerosis, hypertonia, circulatory system disease, and hyperphagia and a pharmaceutical composition obtained by using them.

5 Claims, 9 Drawing Sheets

FIG. 1

```
      -908 CTTCTAGGCCAGAGCTGGGTTCCACAAGAGACAGAATAGG    -868

CATATATATGCTTAAGGAACTGGAAAAACAGGCTCTCTCTCTCACAAA    -818

CACACACACACACATACCAAGGTAGCTGTCAAAATGTTATCCGAAATTTT    -768

GGAACCAAAAAATCTTGAAAGATGGTATTCCAATATCACATTTTATGTAA    -718

GTTTTCTATTATATTAGATTCAAATTACGATTCGAGGCCACAAGCTTTAA    -668

GAATTCAGGGCCTTTTTAACTTGCCAAGCCCCACACCACTCCAGGAACTT    -618

CCCCACACCCCAGTTCTCAGAATTCATGTGCAAGGTCTTTCCTAAATCCA    -568

GGGTCCAGGTCAGAGAGTGGAGGATGTGCTCTATTTCTTACCTGATTGCA    -518

GACCCCTCTGACAGTGCTCCCTTCTGAAGCACTCACTGTCTGAACGTACA    -468

CAGTCTCAGACTTAATCATGCACAGTGAGCAAGACTGTGGTGTGATAATT    -418

GGCGTCCCTGACTTATTAGGGCAAATCTATGGGAGGGGGAGACCTCCTGG    -368

ACCACTGAGCAATTAATTCATTTACATTAGGAAGTTTCTCCGTCAGATGC    -318

AGGAAAAAAATCTTGTTTTCCTGCTGTGGTTTTGACTTTTGCCCCATCTT    -268
                                    -285        -273
                                      | PPRE |

CTGTTGCTGTTGTAGGAGGCAAAATAAGGGTCAAGGCCTGGAAACACAAG    -218
                                    -237     -229
                                     | LRH-RE |

TGCTTTGACTGAAGCTCCACTTGGCTTCCGAAGCCCAAGCTGGGTTGTAC    -168

CAGGTTCCCTAGGGTGCAGGCTGTGGGCAACTGCCAGGGACATGTGCCTG    -118

CCCACCGGCCTCTGGCCCTCACTGAGTTGGCCAATGGGAAATGACAATTG    -68

TGAGGTGGGGACTGCCTGCCCCCGTGAGTACCAGGCTGTTGAGGCTGGGC    -18

CATCTCCTCCTCACTTC / CATTCTGACTGCAG                  +14
                     -1  +1
```

FIG. 2

STRUCTURE OF HUMAN ADIPONECTIN
PROMOTER/REPORTER PLASMID

TRANSCRIPTIONAL
STARTING POINT

-908                    +1  +14
━━━━━━━━━━━━━━━━━━━━━━━┗▶[LUC]  p (-908)/LUC

HUMAN ADIPONECTIN PROMOTER

DELETION CONSTRUCTS OF
HUMAN ADIPONECTIN PROMOTER

-380            +14
━━━━━━━━━━━━━━━┗▶[LUC]  p (-380)/LUC

-337            +14
━━━━━━━━━━━━━┗▶[LUC]  p (-337)/LUC

-286            +14
━━━━━━━━━━━┗▶[LUC]  p (-286)/LUC

-267            +14
━━━━━━━━━━┗▶[LUC]  p (-267)/LUC

-174            +14
━━━━━━┗▶[LUC]  p (-174)/LUC

FIG. 5

| GENE | PPRE SEQUENCE |
|---|---|
| HUMAN ADIPONECTIN | 5'-GGGGCA A AAGTCA-3' |

| GENE | PPRE SEQUENCE |
|---|---|
| MOUSE aP2 | 5'-GGGTGA A ATGTGC-3'<br>5'-GGATCA G AGTTCA-3' |
| MOUSE c-Cbl BINDING PROTEIN | 5'-AGGCTA A AGGTCA-3' |
| MOUSE LXRα | 5'-GGGGCA A AGTTCA-3' |
| MOUSE AQUAPORIN ADIPOSE | 5'-AGGGGA G AGGTCA-3' |

FIG. 6

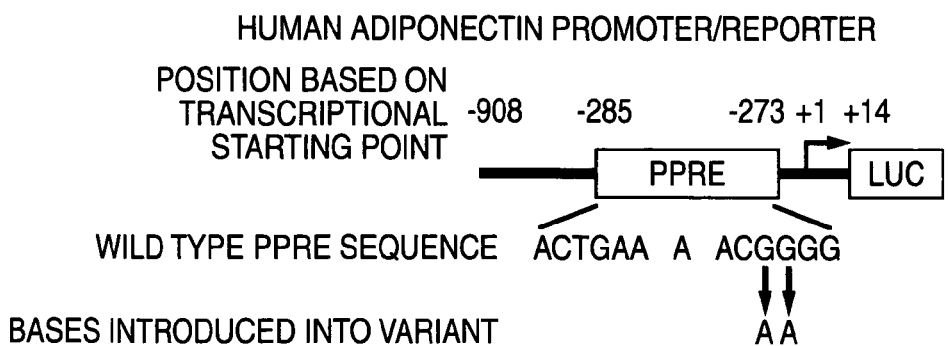

HUMAN ADIPONECTIN PROMOTER/REPORTER

POSITION BASED ON TRANSCRIPTIONAL STARTING POINT: -908   -285    -273 +1 +14

WILD TYPE PPRE SEQUENCE   ACTGAA A ACGGGG

BASES INTRODUCED INTO VARIANT   A A

NUCLEAR RECEPTORS   PPARγ   -  +  -  +  +  +  +  +
SYNTHESIZED IN VITRO RXRα   -  -  +  +  +  +  +  +

COMPETITIVE OLIGO DNA  -  -  -  -  PPRE wt X10  PPRE wt X50  PPRE mut X10  PPRE mut X50

LANE 1 2 3 4 5 6 7 8

| GENE | LRH-RE SEQUENCE |
|---|---|
| HUMAN ADIPONECTIN | 5'-TCAAGGCCT-3' |
| RAT CYP7A1 | 5'-TCAAGGCCG-3' |
| HUMAN CYP7A1 | 5'-TCAAGGCCA-3' |
| HUMAN CETP | 5'-GCAAGGTCC-3' |
| RAT CYP8B1 | 5'-GCAAGGTCC-3'<br>5'-CCAAGGGCA-3' |

ADIPONECTIN PROMOTER AND USE THEREOF

TECHNICAL FIELD

The present invention relates to a promoter containing novel regulatory nucleotide sequences for gene expression and use thereof. Concretely, it relates to a DNA containing the promoter region with regulatory sequences of human adiponectin gene, transformants transformed with the DNA, and screening methods of compounds or salts thereof that accelerate adiponectin promoter activity via the regulatory sequences.

BACKGROUND ART

Recently, the adipose tissue has been shown to be an endocrine organ that actively produces and secretes many bioactive substances, called adipocytokines, which play a crucial role in the control of systemic glucose and lipid metabolism (*Nature*, 414:799-806, 2001). Adiponectin is one of adipocytokines identified as the most abundantly-expressing gene in human adipocytes and as a hormone (*Biochemical and Biophysical Research Communication*, 221:286-289, 1996). Adiponectin is specifically produced and secreted in adipocytes, and exists abundantly in the blood.

Many research results have shown that adiponectin is an antidiabetic, antiarteriosclerotic, and antiobestic hormone, which is closely associated with the onset and progress of metabolic diseases. For example, plasma adiponectin concentration was decreased in patients with ischemic heart diseases or insulin-resistant diabetes (*Circulation*, 100:2473-2476, 1999; *Arteriosclerosis, Thrombosis, and Vascular Biology*, 20:1595-1599, 2000). Furthermore, in patients with mutations in the adiponectin gene, the decrease in plasma adiponectin concentration was associated with the onset of insulin-resistant diabetes or atherosclerosis (*Diabetes*, 50: 1126-1133, 2002). In obese diabetic monkeys, the progressive reduction in plasma adiponectin was deeply associated with the aggravation of insulin resistance (*Diabetes*, 50:1126-1133, 2001). In adiponectin-deficient mice, diabetes was caused by the load of high sucrose and high fat diet, and neointimal thickening after artery injury was remarkably accentuated. Adenovirus-mediated supplement of adiponectin into the knockout mice eminently improved the lesion (*Nature Medicine*, 8:731-737, 2002, *Journal of Biological Chemistry*, 277:37487-37491, 2002). Moreover, adenoviral supplement of adiponectin into apolipoprotein E-deficient mice suppressed the progress of arteriosclerosis (*Circulation*, 106:2767-2770, 2002). When recombinant adiponectin protein was administrated in metabolically-impaired mice, the improvement of insulin resistance and hypoglycemic action were seen (*Nature Medicine*, 7:941-946, 2001, *Nature Medicine*, 7:947-953, 2001). According to these facts, the therapy raising plasma adiponectin concentration is thought to be effective in improving the condition of patients with hypoadiponectinemia. However, plasma adiponectin concentration in human, which is 5-20 µg/ml (*Biochemical and Biophysical Research Communication*, 257:79-83, 1999), is extremely high compared with other blood hormones. Considering this respect, in patients with hypoadiponectinemia, it is thought that the substitution therapy of recombination adiponectin protein to normalize plasma concentration would be accompanied by various great difficulties in continuous high-dose administration of the protein or the prevention of in vivo enzymatic hydrolysis of the protein.

DISCLOSURE OF THE INVENTION

Though the production of proteins can be controlled at various stages in vivo, the transcriptional regulation is the most fundamental step. Thus, modifying the level of disease-associated protein at the transcriptional stage is one of the powerful means to treat diseases. Gene transcription is regulated via the promoter and enhancer region located in neighborhood of the nucleotide sequence transcribed into messenger RNA. For transcriptional regulation, a kind of proteins, called transcriptional regulatory factors, is needed to bind to the nucleotide sequences, called the regulatory sequences, in the promoter and enhancer regions of the gene. Among those transcriptional regulatory factors, a group of proteins called nuclear receptors have a unique character that their activities can be regulated by interacting with small molecules called ligands. For example, PPARγ (peroxisome proliferator-activated receptor γ) is an important nuclear receptor for adipose differentiation. PPARγ forms a heterodimer with another nuclear receptor RXR (retinoid X receptor) and specifically binds to the regulatory sequence called PPRE (peroxisome proliferator-activated receptor responsive element) in the promoter or enhancer region of the genes. PPARγ activity is regulated by endogenous unknown ligands or exogenous ligands such as thiazolidinedione derivatives (*Annu. Rev. Biochem.*, 70:341-367, 2001). The regulatory sequence PPRE is comprised of the characteristic nucleotide sequence that is represented by 5'-AGGTCAnAGGTCA-3' (SEQ ID NO:15), which is different from every kind of genes with PPRE. When creating the medicine that can exhibit efficacy by changing the adiponectin production at the transcriptional stage, identification of the regulatory sequence in the promoter or enhancer region of the adiponectin gene is quite useful in constructing the efficient and best screening system for discovering potential compounds. Transformants can be created by connecting a DNA containing the identified regulatory sequences to a suitable reporter gene, and transforming host cells with the DNA. The transformants can be used as a useful screening system of preventive and/or therapeutic medicines for metabolic disorder such as diabetes, obesity, hypercholesterolemia, and hyperlipoproteinemias, etc., hyperlipidemia, arteriosclerosis, hypertonia, circulatory system disease, and hyperphagia, etc., which can act through the induction of adiponectin gene expression. Moreover, the transformants can be also used as the useful screening system of preventive and/or therapeutic medicines for various syndromes (Syndrome X, metabolic syndrome, multiple risk factor syndrome, insulin resistance syndrome, deadly quartet, visceral fat syndrome, etc.) caused by the above diseases. However, regulatory sequences related to the control of human adiponectin gene expression has not been identified so far and no method can substantially and effectively screen any accelerators of the human adiponectin gene expression.

As a result of the present inventors' repeated researches to establish the screening method that can explore accelerators of the adiponectin gene expression, they discovered and identified the characteristic regulatory sequence PPRE and LRH-RE (liver receptor homologue-1 responsive element) of adiponectin gene in the 5' upstream promoter region of human adiponectin gene. Moreover, they found that PPRE and LRH-RE modulate the physiological human adiponectin promoter activity. According to these findings, the present inventors have completed this invention as a result of more researches.

That is, the present invention relates to the followings:
(1) A DNA comprising a promoter region having the nucleotide sequence presented by SEQ ID NO:1 which comprises a regulatory sequence of a human adiponectin gene.
(2) The DNA according to the above (1), which consists of a promoter region having the nucleotide sequence presented by SEQ ID NO:1 which comprises a regulatory sequence of a human adiponectin gene.
(3) The DNA according to the above (2), wherein the regulatory sequence is a sequence containing PPRE (Peroxisome Proliferator-activated Receptor Responsive Element).
(4) The DNA according to the above (2), wherein the regulatory sequence is a sequence containing LRH-RE (Liver Receptor Homologue-1 Responsive Element).
(5) The DNA according to the above (2), wherein the regulatory sequence is the nucleotide sequence presented by SEQ ID NO:2.
(6) he DNA according to the above (2), wherein the regulatory sequence is the nucleotide sequence presented by SEQ ID NO:3.
(7) The DNA according to the above (2), wherein the regulatory sequence is a nucleotide sequence comprising the nucleotide sequence presented by SEQ ID NO:2 and the nucleotide sequence presented by SEQ ID NO:3.
(8) The DNA according to the above (2), which the regulatory sequence is the nucleotide sequence presented by SEQ ID NO:4.
(9) A recombinant plasmid DNA comprising the DNA according to the above (2).
(10) The recombinant plasmid DNA according to the above (9), which is capable of expressing a structural gene under control of the promoter region comprising the regulatory sequence of human adiponectin gene can express.
(11) A transformant transformed with the recombinant plasmid DNA according to the above (9) or (10).
(12) A screening method of a compound which is capable of enhancing human adiponectin promoter activity or a salt thereof, which comprising using the transformant according to the above (11).
(13) A screening method of a preventive and/or therapeutic medicine for syndromes selected from syndrome X, metabolic syndrome, multiple risk factor syndrome, insulin resistance syndrome, deadly quartet, and visceral fat syndrome, which comprises using the transformant according to the above (11).
(14) The screening method according to the above (13), which a disorder as a etiology of the syndrome is diabetes, obesity, hypercholesterolemia, hyperlipoproteinemias, hyperlipidemia, arteriosclerosis, hypertonics, circulatory system disease, or polyphagies.
(15) A screening kit of a compound which is capable of enhancing human adiponectin promoter activity or a salt thereof, which comprises using the transformant according to the above (11).
(16) A screening kit of a preventive and/or therapeutic medicine for syndrome selected from syndrome X, metabolic syndrome, multiple risk factor syndrome, insulin resistance syndrome, deadly quartet, and visceral fat syndrome, which comprises using the transformant according to the above (11).
(17) A compound which is capable of enhancing human adiponectin promoter activity or a salt thereof, which is obtainable by using the screening method according to the above (12).
(18) A preventive and/or therapeutic medicine for syndrome selected from syndrome X, metabolic syndrome, multiple risk factor syndrome, insulin resistance syndrome, deadly quartet, and visceral fat syndrome, which is obtainable by using the screening method according to the above (13).
(19) A compound which is capable of enhancing human adiponectin promoter activity or a salt thereof, which is obtainable by using the screening kit according to the above (15).
(20) A preventive and/or therapeutic medicine for syndromes selected from syndrome X, metabolic syndrome, multiple risk factor syndrome, insulin resistance syndrome, deadly quartet, and visceral fat syndrome, which is obtainable by using the screening kit according to the above (16).
(21) A pharmaceutical composition which comprises the compound which is capable of enhancing human adiponectin promoter activity according to the above (17) or (19) or a salt thereof.
(22) A pharmaceutical composition which comprises the preventive and/or therapeutic medicine for syndromes selected from Syndrome X, metabolic syndrome, multiple risk factor syndrome, insulin resistance syndrome, deadly quartet, and visceral fat syndrome according to the above (18) or (20).

The DNA of the present invention containing the regulatory sequence PPRE or LRH-RE in the promoter region of human adiponectin gene or containing both PPRE and LRH-RE may be anything as long as it contains the regulatory sequence and has the adiponectin promoter activity. Concretely, it may be anything as long as it contains the nucleotide sequence presented by SEQ ID NO:1, the complimentary sequence, or these parts. Moreover, it may be anything of genomic DNA, cDNA, and a synthetic DNA derived from human.

Concretely, the DNA that contains the regulatory sequence PPRE and/or LRH-RE in the promoter region of human adiponectin gene of the present invention can be obtained as follows.

Firstly, using primers corresponding to the nucleotide sequence of the promoter region of human adiponectin gene that has already been reported (*Int. J. Obes. Relat. Metab. Disord.,* 24:861-868, 2000), target DNA fragments are amplified by PCR method using genomic DNA (for example, clontech) derived from human tissues as template. The obtained DNA may be cloned into plasmid and the nucleotide sequence may be determined. According to the purpose, the obtained DNA may be used as it is, being digested by restriction enzymes, or being ligated to linkers. Moreover, a method of connecting a transcriptionally detectable reporter gene to the downstream of the obtained DNA is preferred as a method to examine the promoter activity. Though luciferase gene, chloramphenicol acetyl transferase gene, alkaline phosphatase gene, and beta-galactosidase gene, etc. are used widely as a reporter gene, even any other structural genes are possible to use it if the gene product can be detected.

As a host for transformation with the above recombinant plasmid DNA, yeasts, insect cells, and animal cells, etc. can be used. For example, yeasts include *Saccharomyces cerevisiae* AH22R⁻, NA87-11A, and DKD-5D, etc. As insect cells, for example, mamestra brassicoe Sf9 cells and silkworm BmN cells, etc. can be used. As animal cells, for example, monkey COS-1 cells, COS-7 cells, Chinese hamster CHO cells, mouse L cells, 293T cells, 3T3-L1 cells, human HEK293 cells, HepG2 cells, albedo adipocytes, and differentiation-induced cells by suitable differentiation condition, etc. can be used.

Yeasts are transformed by a properly modified method that is described in, for example, *Proc. Natl. Acad Sci. USA,* vol. 75, 1929 (1978). Insect cells are transformed by a properly modified method that is described in, for example, *Bio/Tech-* nology, vol. 6, 47, (1988), etc. Animal cells are transformed by a properly modified method that is described in, for example, *Cell Technology suppl.8/New Cell Technology Experimental Protocol*, 263 (Issued from Shujunsha Co. Ltd. in 1995.) and Virology, vol. 52, 456 (1973), etc.

By culturing the above transformants under the presence of a specific compound and comparing the measured amounts of the gene product in the preparation, its capacity to stimulate the promoter activity can be known. The transformants can be cultured by a method well-known in itself.

When the hosts for transformants are yeasts, for example; Berkholder-minimum medium (*Proc. Natl. Acad. Sci. USA*, vol.77, 4505 (1980)) is enumerated as a culture medium. The medium is suitably adjusted to approx pH 5 to 8. It is usually cultured for approx 24 to 72 hours at approx 20 to 30° C., and is ventilated and is stirred, if necessary.

When the hosts for transformants are insect cells, the additive such as 10% inactivated bovine serum, etc. is properly added to Grace's Insect Medium (*Nature*, vol. 195, 788 (1962)). The medium is suitably adjusted to approx pH 6.2 to 6.4. It is usually cultured for approx 3 to 5 days at approx 27° C. and is ventilated and is stirred, if necessary.

When the hosts for transformants are animal cells, for example, Dulbecco's modified Eagle medium (Nacalai Tesque, Inc.) containing approx 5-20% of the fetal bovine serum is used as a culture medium. The medium is suitably adjusted to approx pH 6 to 8. It is usually cultured for approx 15 to 60 hours at approx 30 to 40° C. and is ventilated and is stirred, if necessary.

Because the DNA of the present invention is a nucleotide fragment including the promoter region that contains either of the regulatory sequence PPRE or LRH-RE in human adiponectin promoter region, or both, a compound or salt thereof that enhances the human adiponectin promoter activity can be screened by using the transformants. As follows, it concretely explains the screening method, the screening kit, and the compound or salt thereof that enhances the promoter activity of human adiponectin gene, which is obtained with the screening method and the screening kit.

(1) The Method Screening the Compound or Salt Thereof That Enhances the Promoter Activity of Human Adiponectin Gene The transformants transformed with the DNA including the promoter region that contains either of the regulatory sequence PPRE or LRH-RE in human adiponectin promoter region or both, are usefull for screening the compound or salt thereof that enhances the promoter activity of human adiponectin gene.

A method to determine whether the compound or salt thereof can enhance the promoter activity of human adiponectin gene is characterized by comparing the amount of polypeptide expression using transformants containing the regulatory sequence of the present invention, with that using transformants without the regulatory sequence.

The subject compounds include peptides, proteins, non-peptide compounds, synthetic compounds, and fermentation products, etc. The compounds may be new compounds and well-known compounds. The polypeptides coded by the above structural genes (suitable reporter genes), etc. are used as the expressed polypeptides. The measuring method of the polypeptide expression includes, for example, measuring the luciferase activity by a method according to Brasier et al.'s method (*Biotechniques*, vol. 7, 1116-1122 (1989)).

(2) The Kit for Screening the Compound or Salt Thereof That Enhances the Promoter Activity of Human Adiponectin Gene The kit of the present invention for screening the compound or salt thereof that enhances the promoter activity of human adiponectin gene is characterized as using the above transformants, and the following are enumerated as the example.

A Cell Culture Medium:
Dulbecco's modified Eagle medium (Nacalai Tesque, Inc.) containing 5% of inactivated fetal bovine serum (JRH Biosciences, Inc.)

A plasmid for measuring the human adiponectin promoter activity: the one of which the DNA containing the regulatory sequence PPRE and LRH-RE in human adiponectin promoter region of the present invention is inserted in multi-cloning site of pGL3-basic vector (Promega corporation) containing a luciferase gene.

A plasmid for nuclear receptor expression: Each full-length cDNA of human PPARγ, human RXRα, and human LRH-1 is obtained by PCR using the human cDNA library (Clontech) as a template. The one of which the obtained cDNA and the expression plasmid for mammalian cells are cut with the same restriction enzymes and connected is used.

Host Cell Lines:
HEK293 cells (human fetal kidney-derived cell lines, obtained from ATCC).

Subject compounds: Before using, the aqueous solution stored at 4° C. or −20° C. is diluted to 50 μM with cell culture medium. Water-insoluble compounds are dissolved with dimethyl sulphoxide and ethanol, etc.

(3) Screening Method

HEK293 cells are seeded into 96-well multiplate (Nalge Nunc International) and are incubated under 5% of $CO_2$, at 37° C., for overnight. Transfection is carried out according to a method described in Lu et al.'s report (*Mol. Cell*, 6:507-515, 2000). 50 ng/well of the plasmid for the measure of promoter activity in human adiponectin promoter of the present invention and 15 ng/well of the plasmid expressing the nuclear receptor are transiently transfected by calcium phosphate method. 8 hours after transfection, subject compound diluent of one-fifth amount of culture supernatant is added. The culture is incubated under 5% of $CO_2$, at 37° C., for 18 hours and then 100 μl/well of Pickagene LT reagent (TOYO INK. CO., LTD.) is added. After stirring for 5 minutes, the luminescence intensity is measured by Lmax microplate luminometer (Molecular Devices corporation).

If a subject compound explored by using the above screening method or the screening kit enhances the promoter activity of human adiponectin gene, it can increase the production and secretion of adiponectin in adipose tissue and thereby increase the plasma adiponectin concentration. Therefore, the compound can be used as a preventive and/or therapeutic medicine for metabolic disorder such as diabetes, obesity, hypercholesterolemia, hyperlipoproteinemia, hyperlipidemia, arteriosclerosis, hypertonia, circulatory system diseases, and hyperphagia, etc.

In addition, the compound can be used as a preventive and/or therapeutic medicine for various syndromes (Syndrome X, metabolic syndrome, multiple risk factor syndrome, insulin resistance syndrome, deadly quartet, visceral fat syndrome, etc.) of which the above disease are an etiology.

Non-toxic salts of the compound obtained by the above screening method or the screening kit include, for example, alkali metal salts (potassium, sodium, lithium, etc.), alkaline earth metal salts (calcium, magnesium, etc.), ammonium salts (tetramethylammonium, tetrabutylammmonium, etc.), organic amine salts (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid-addition salts (inorganic acid salts (hydrochloride, hydrobromate, hydroiodate, sulfate, phosphate, and nitrate, etc.), and organic acid salts (acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc.), etc.

Non-toxic salts of the compound in the present invention also include solvates thereof, or solvates of alkali (earth) metal salts, ammonium salts, organic amine salts, and acid-addition salts of the above compound in the present invention.

The solvates are preferably non-toxic and water-soluble. Appropriate solvates, for example, solvates such as water, alcohol solvents (ethanol, etc.), etc. are included.

When the compound of the present invention or salt thereof is used as the preventive or therapeutic medicine, it is used as a solid preparation and a liquid medicine for oral administration, and injections, external preparations, and suppositoriums, etc. for parenteral administration.

The solid composition for oral administration includes a tablet, a pill, a capsule, a dispersing powder, a granule, etc. The capsule includes a hard capsule and a soft capsule.

In such solid composition, an active compound is used by being formulated according to usual methods as it is, or by being mixed with inert diluents (lactose, mannitol, glucose, hydroxypropyl cellulose, microcrystalline cellulose, starch, etc.), binders (hydroxypropylcellulose, polyvinyl pyrrolidone, and magnesium aluminometasilicate, etc.), disintegrators (calcium carboxymethylcellulose, etc.), lubricants (magnesium stearate etc.), stabilizers, and solubilizers (glutamate and aspartic acid, etc.). It may be coated with coating agents (sugar, gelatin, hydroxypropyl cellulose or hydroxypropyl cellulose phthalate, etc.) or be coated with two or more films, if necessary. Furthermore, it includes a capsule comprising of absorbable material such as gelatin.

The liquid composition for oral administration includes pharmaceutically acceptable emulsions, solutions, syrups and elixirs. In such liquid composition, an active compound is dissolved, suspended, and emulsified in general inert diluents (purified water, ethanol, and mixture thereof, etc.). Furthermore, this liquid composition may also contain wetting agents, suspending agents, emulsifying agents, sweetening agents, flavoring agents, perfuming agents, preserving agents, and buffer agents, etc.

The injection for parenteral administration includes solutions, suspensions, emulsions, and solid injections that are dissolved or suspended in a solvent before using. The injection is used by dissolving, suspending, or emulsifying an activator into a solvent. For example, distilled water for injection, saline, vegetable oil, alcohols such as propylene glycol, polyethyleneglycol, and ethanol, and the combination thereof is used as a solvent. Furthermore, this injection may include stabilizers, solubilizers (glutamic acid, aspartic acid, POLYSORBATE 80®, suspending agent, emulsifying agents, soothing agents, buffer agents, and preservatives, etc. These are manufactured by being sterilized or the aseptic manipulation in the final process. The sterile solid preparation can be used by being manufactured as a freeze-dried preparation, and being sterilized or dissolved in distilled water for injection or other solvent before using.

The external preparation for parenteral administration includes, for example, ointments, gels, creams, fomentations, patches, embrocations, aerosols, inhalants, sprays, aerosols, eye drops, and nasal drops, etc. These include an activator and are manufactured by the well-known method or the formula usually used.

The ointment is manufactured by the well-known method or the formula usually used. For example, it is manufactured by mixing and melting the activator into a basis. The ointment base is chosen from the well-known one or the one usually used. For example, they are used alone or by being mixed with two or more kinds chosen from higher fatty acid, higher fatty acid ester (adipic acid, myristic acid, palmitic acid, stearic acid, oleic acid, adipic acid ester, myristic acid ester, palmitate, stearic acid ester, and oleic acid ester, etc.), waxs (yellow wax, spermaceti, and ceresin, etc.), surfactants (polyoxyethylene alkyl ether phosphate etc.), higher alcohols (cetanol, stearyl alcohol, and cetostearyl alcohol, etc.), silicone oils (dimethylpolysiloxane etc.), hydrocarbons (hydrophilic petrolatum, white petrolatum, purified lanolin, and liquid paraffin, etc.), glycols (ethylene glycol, diethylene glycol, propylene glycol, polyethylene glycol, and macrogol, etc.), vegetable oils (castor oil, olive oil, sesame oil, and oil of turpentine, etc.), animal oils (mink oil, yolk oil, squalane, and squalene, etc.), water, absorption enhancer, and poisoned inhibitor. Further, they may include moisturizing agents, preservatives, stabilizing agents, anti-oxidants, and flavors, etc.

The gel is manufactured by the well-known method or the formula usually used. For example, it is manufactured by melting an activator into a basis. The gel base is chosen from the well-known one or the one usually used. For example, it is used alone or by being mixed with two or more kinds chosen from lower alcohols (ethanol and isopropyl alcohol, etc.), gelatinizers (carboxymethylcellulose, hydroxyethyl cellulose, hydroxypropylcellulose, and ethyl cellulose, etc.), neutralizers (triethanolamine and diisopropanolamine, etc.), surfactants (mono-stearic acid polyethylene glycol, etc.), gums, water, absorption enhancers, and poisoned inhibitors. Further, it is include preservatives, anti-oxidants, and flavors, etc.

The cream is manufactured by the well-known method or the formula usually used. For example, it is manufactured by melting or emulsifying an activator into a basis. The cream base is chosen from the well-known one or the one usually used. For example, they are used alone or by being mixed with two or more kinds chosen from higher fatty acid esters, lower alcohols, hydrocarbons, polyhydric alcohols (propylene glycol, 1,3-butylene glycol, etc.), higher alcohols (2-hexyl decanol and cetanol, etc.), and emulsifiers (polyoxyethylene alkyl ethers and fatty acid esters, etc.), water, absorption enhancers, and poisoned inhibitors. Further, it may include preservatives, anti-oxidants, and flavors, etc.

The fomentation is manufactured by the well-known method or the formula usually used. For example, it is manufactured by melting an activator into a basis and spreading it and rolling on the support after kneading. The fomentation base is chosen from the well-known one or the one usually used. For example, they are used alone or by being mixed with two or more kinds chosen from thickeners (polyacrylic acid, polyvinyl pyrrolidone, arabic gum, starch, gelatin, and methyl cellulose, etc.), humectants (urea, glycerin, and propylene glycol, etc.), and fillers (china clay, flower of zinc, talc, calcium, and magnesium, etc.), water, absorption enhancers, and poisoned inhibitors. Further, it may include preservatives, anti-oxidants, and flavors, etc.

The patch is manufactured by the well-known method or the formula usually used. For example, it is manufactured by melting an activator into a basis and spreading it and rolling on the support after kneading. The patch base is chosen from the well-known one or the one usually used. For example, they are used alone or by being mixed with two or more kinds chosen from high molecular basis, oils, fats, higher fatty acids, tackifiers, and poisoned inhibitors. Further, it may include preservatives, anti-oxidants, and flavors, etc.

The liniment is manufactured by the well-known method or the formula usually used. For example, it is manufactured by dissolving, suspending, or emulsifying an activator into alone, or two or more kinds chosen from water, alcohols (ethanol and polyethylene glycol, etc.), higher fatty acids, glycerins, soaps, emulsifiers, suspending agents, etc. Further, it may include preservatives, anti-oxidants, and flavors, etc.

The aerosol, the inhalant, and the spray may contain stabilizers such as sodium hydrogen sulfite, buffers giving isotonicity, and isotonic agents such as, for example, sodium chloride, sodium citrate, and citrates besides the general diluent. Production methods of the spray have been described in U.S. Pat. Nos. 2,868,691 and 3,095,355.

Usually, the nasal drop is quantitatively spray-administered into the nasal cavity as a solution and a powder containing a medicine or by using the dedicated nasal drip machine or the sprayer.

The eye drop for parenteral administration includes eye drops, eye suspensions, eye emulsions, dissolution type of eye solutions before using, and eye ointment.

For example, they are used by dissolving, suspending, and emulsifying an activator into a basis. As a solvent of eye drop, for example, sterile purified water, saline, other water solvent, or injectable nonaqueous solvent (for example, vegetable oil etc.), and combination thereof are used.

For example, the ophthalmic solutions are made with tonicity agents (sodium chloride and concentrated glycerin, etc.), buffers (sodium phosphate and sodium acetate, etc.), surfactants (polysorbate 80 (trade name), polyoxyl 40 stearate, and polyoxyethylene hydrogenated castor oil, etc.), stabilizers (sodium citrate and disodium edetate, etc.), and preservatives (benzalkonium chloride and paraben, etc.), etc., which are properly selected, if necessary. These are sterilized in the final process or manufactured by the aseptic manipulation. The manufactured sterile solid preparation, for example, freeze-drying product can be used by being sterilized or being dissolved to sterile purified water or other sterile solvent before using.

Inhalants for parenteral administration may include aerosol agents, inhalant powders or inhalant liquids, which may be used by being dissolved or suspended in water or other suitable media before using. These inhalants are manufactured according on a well-known method. For example, inhalant liquids are prepared by being properly selected from preservatives(benzalkonium chloride and paraben, etc.), coloring agents, buffers (sodium phosphate and sodium acetate, etc.), tonicity agents (sodium chloride and concentrated glycerin, etc.), thickeners (carboxyvinyl polymer, etc.), and absorption enhancers, etc., if necessary.

Inhalant powders are prepared by being properly selected from lubricants (stearic acid and the salt, etc.), binders (starch and dextrin, etc.), fillers (lactose and cellulose, etc.), coloring agents, preservatives (benzalkonium chloride and paraben, etc.), and absorption enhancers, etc., if necessary.

When the inhalant liquid is administered, a sprayer (atomizer and nebulizer) is usually used, and when the inhalant powder is administered, an inhalation administering machine for powder is usually used.

As other compositions for parenteral administration, suppositories for intrarectal administration, and pessaries for administering in vagina, which contain activators and are prescribed with common procedure, are included.

Because the obtained preparations in this way are safe and low-toxic, they can be administered to, for example, human and mammals (for example, rat, mouse, rabbit, cat, dog, and monkey, etc.). The dosage is determined depending on age, body weight, symptom, therapeutic effect, administration route, duration of the treatment and the like. Generally, 1 ng to 100 mg per an adult is orally administered once to several times per a day, or 0.1 ng to 10 mg per an adult is parenterally administered (preferably, nosedrop, ophthalmic solution, ointment) once to several times per a day, or intravenously administered for 1 to 24 hours per a day, continuously.

Since the dose changes depending on various conditions as described above, there are also cases in which doses lower or greater than the above dose may be used.

BRIEF DESCRIPTION OF THE DRAWINGS

FIG. 1 shows the DNA sequence containing human adiponectin promoter region;

FIG. 2 shows the structure of human adiponectin promoter/reporter plasmid. DNA and promoter-deletion constructs;

FIG. 5 shows comparison of PPRE nucleotide sequences of the genes that are transcriptionally regulated by PPARγ/RXR heterodimer, where the human adiponectin PPRE sequence is SEQ ID NO:16, where the mouse aP2 PPRE sequences are SEQ ID NO:17 (upper) and SEQ ID NO:18 (lower), where the mouse c-Cb1 binding protein PPRE sequence is SEQ ID NO:19, where the mouse LXRαPPRE sequence is SEQ ID NO:20, and where the mouse aquaporin adipose PPRE sequence is SEQ ID NO:21;

FIG. 6 shows PPRE sequence (SEQ ID NO:22) in human adiponectin gene and a structure of human adiponectin promoter/reporter plasmid DNA mutated in PPRE sequence;

BEST MODE FOR CARRYING OUT THE INVENTION

The following examples illustrate the present invention, but do not limit the present invention.

EXAMPLE 1

Construction of Human Adiponectin Promoter/Reporter Plasmid DNA

A DNA containing human adiponectin promoter region was amplified by PCR method using DNA fragments obtained according to Takahashi et al.'s method as a template (*Int. J. Obes. Relat. Metab. Disord.*, 24, 861-868 (2000)). Concretely, a clone containing human adiponectin gene was obtained from human P1-derived artificial chromosome (PAC) DNA pool (GENOMESYSTEMS, INC.), and was digested by restriction enzymes BamHI and XbaI. 2.9 kb of the DNA fragments among the obtained fragments contained the 5'-upstream region of human adiponectin gene (*Int. J. Obes. Relat. Metab. Disord.*, 24, 861-868 (2000)). Using the DNA fragments as a template and primers (5'-TTT CGG GGT ACC GCT TCT AGG CCA GAG CTG GGT TC-3' (SEQ ID NO:5) and 5'-TTT CGG GAG CTC CTG CAG TCA GAA TGG AAG TGA GAA-3' (SEQ ID NO:6)), the DNA fragments containing human adiponectin promoter region were amplified, and the nucleotide sequence was determined. FIG. 1 shows the nucleotide sequence. The amplified DNA fragments and pGL3 basic plasmid (Promega Corporation) having firefly luciferase gene were digested by restriction enzymes KpnI and SacI, and both were ligated. FIG. 2 shows the schematic structure. Hereafter, this human adiponectin promoter/reporter plasmid is abbreviated as p(−908)/LUC.

EXAMPLE 2

Figure 3:
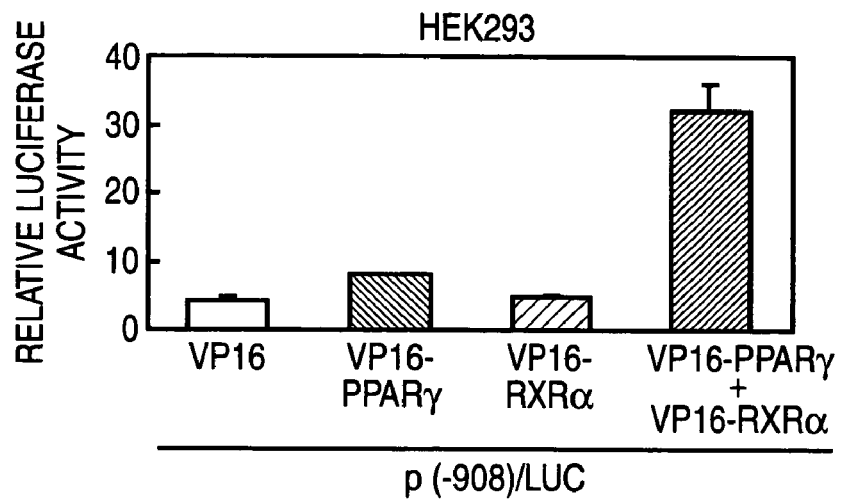
FIG. 3 shows transcriptional activities of human adiponectin promoter/reporter plasmid DNA enhanced by constitutively-active PPARγ and RXRα.

Assay of Transcriptional Activities of Human Adiponectin Promoter/Reporter Plasmid DNAs Luciferase assay was performed using p(−908)/LUC constructed as described in Example 1 and constitutively-active PPARγ/RXR heterodimer. By transfection of expression plasmid encoding each chimera nuclear receptor (they are abbreviated as VP16-PPARγ and VP16-RXRα.) of which a transcriptional active region of herpes virus protein VP16 has been linked to nuclear receptor PPARγ or RXRα, the promoter activity was assayed. These chimera nuclear receptors are active the transcription of a responsive gene even in the absence of each ligand (*Mol. Endocrinol.*, 16, 1040-1048 (2002)). As a reporter plasmid, p(−908)/LUC constructed in Example 1 was introduced together with the nuclear receptor expression plasmids. HEK293 cells derived from human fetus kidney were used as a host cell. The cells were seeded into 96-well:multiplate (Nalge Nunc International) and were cultured in Dulbecco's modified Eagle medium (Nacalai Tesque, Inc.) containing 5% of inactivated fetal bovine serum under 5% of $CO_2$, at 37° C., for overnight, and were transformed. Transfection was performed as described in Lu et al.'s report (*Mol. Cell*, 6, 507-515 (2000)). 50 ng per well of the reporter plasmid p(−908)/LUC, 20 ng per well of beta-galactosidase expression plasmid, and 15 ng of each nuclear receptor expression plasmid were respectively transfected by calcium phosphate method. Luciferase activity and beta-galactosidase activity as internal standard were respectively measured by using Lmax microplate luminometer and Emax microplate reader (Molecular Devices corporation) 26 hours after transfection. The result was presented as a relative activity that divides the luciferase activity with the beta-galactosidase activity. FIG. 3 shows the result. In cells expressing both VP16-PPARγ and VP16-RXRα, the remarkable increase in luciferase activity was seen. When only VP16, VP16-PPARγ, or VP16-RXR was expressed, no change was seen. According to these results, it was thought that PPARγ/RXR heterodimer could act on human adiponectin promoter.

EXAMPLE 3

Identification of Regulatory Sequences in Human Adiponectin Promoter Region (PPRE)

Figure 4:
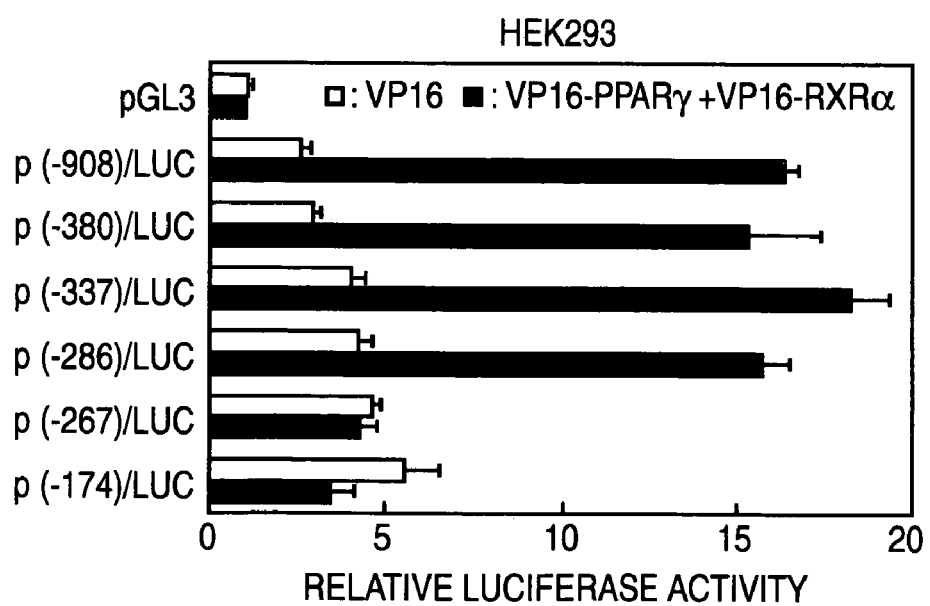
FIG. 4 shows transcriptional activities of human adiponectin promoter/reporter plasmid DNAs and promoter-deletion constructs.

To identify the region in human adiponectin promoter leading to the increase in the transcriptional activity observed in Example 2, deletion constructs of human adiponectin promoter were made as shown at the bottom of FIG. 2. By PCR method using the above p(−908)/LUC as a template and primers designed to obtain a target length of the promoter, the deletion promoter fragment was amplified. The amplified DNA fragments and pGL3 basic plasmid were digested by restriction enzymes and connected. By using each deletion construct as a reporter and transiently expressing both expression plasmids of VP16-PPARγ and VP16-RXRα in HEK293 cells, the luciferase activity was measured as previously described in Example 2. FIG. 4 shows the result. By deleting a sequence from −286 bp to −267 bp in human adiponectin promoter, the increase in luciferase activity by VP16-PPARγ and VP16-RXRα disappeared. As a result, it was presumed that the regulatory sequence PPRE should exist between −286 bp and −267 bp in human adiponectin promoter region.

Figure 7:
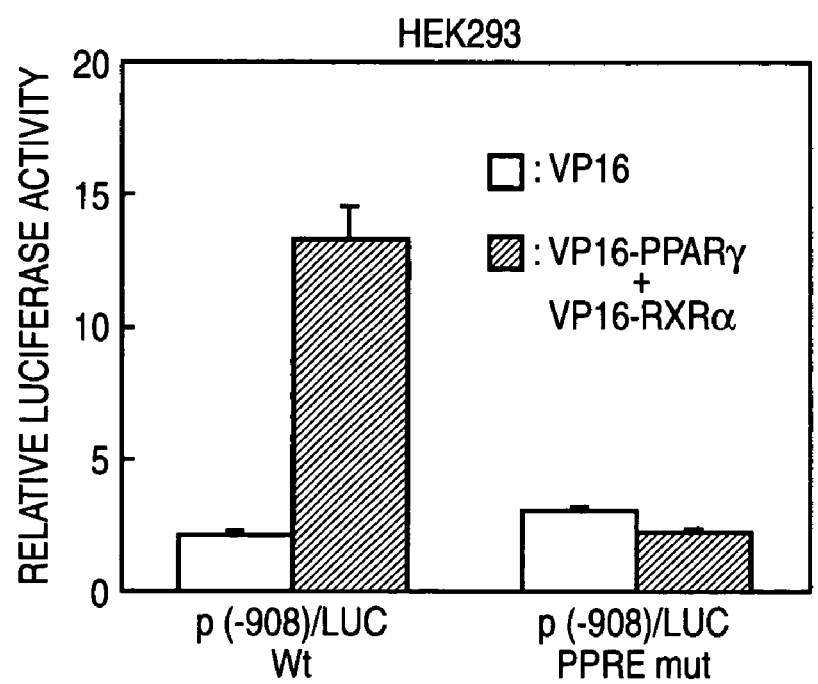
FIG. 7 shows transcriptional activities of the mutated promoter/reporter plasmid DNAs by constitutively-active PPARγ and RXRα.

FIG. 5 shows the nucleotide sequence of PPRE in the promoter region of genes that has been reported to be transcriptionally controlled by PPARγ/RXR heterodimer (*Genes Dev.*, 8, 1224-1234 (1994), *J. Biol Chem.*, 275, 9131-9135 (2000), *Mol. Cell*, 7, 161-171 (2001), *J. Biol. Chem.*, 276, 48572-48579 (2001)). All sequences have a similar structure comprising of 13 bases called "direct repeat 1(DR1)". By examining the nucleotide sequence from −286 bp to −267 bp in human adiponectin promoter region in detail, it turned out that a sequence similar to the reported PPRE existed from −273 bp to −285 bp (FIGS. 5 and 6). To confirm that the presumed sequence functions as the regulatory sequence PPRE, a 2-bp mutation was introduced into a presumed sequence of the reporter plasmid as shown in FIG. 6. The mutation was introduced using QuikChange Site-Directed Mutagenesis kit (Stratagene Corporation) according to a supplyer's protocol. To compare the transcriptional activity of a PPRE-mutant reporter plasmid with that of a wild-type reporter, the luciferase activity was measured as previously described in Example 2. FIG. 7 shows the result. Using a mutated reporter plasmid, the increase in luciferase activity disappeared. The result suggested that the sequence presumed to be PPRE could function as a regulatory sequence and could be necessary for the transcriptional activation of human adiponectin promoter by PPARγ/RXR heterodimer.

EXAMPLE 4

Direct Binding to the Regulatory Sequence PPRE of PPARγ/RXR Heterodimer

Figures 8, 9:
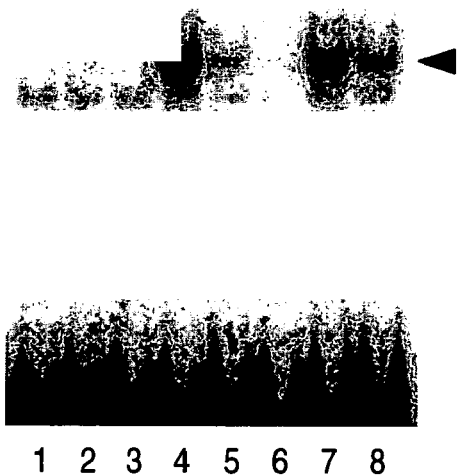
FIG. 8 shows direct binding (gel shift assay) of PPARγ/RXR heterodimer to the regulatory sequence PPRE of human adiponectin promoter.
FIG. 9 shows comparison of LRH-RE nucleotide sequences contained in the genes that are transcriptionally regulated by LRH-1.

To confirm the direct binding of PPARγ/RXR heterodimer to the regulatory sequence PPRE that had been identified from −285 bp to −273 bp in human adiponectin promoter region, gel shift assay was performed according to the method previously described (*J. Biol. Chem.*, 276, 48572-48579 (2001)). For the binding reaction, human PPARγ and RXRα protein were synthesized in vitro by using TNT T7 Quick Coupled Transcription/Translation Systems (Promega corporation) according to a supplyer's protocol. For a labeled probe, oligoDNAs (5'-TGG TTT <u>TGACTTTTGCCCC</u>AT CTT C-3' (SEQ ID NO:7) and 5'-GAA GAT GGGGCAAAAGTCAAACCA-3' (SEQ ID NO:8)) having a nucleotide sequence from −291 bp to −267 bp in human adiponectin promoter region were labeled using [γ-32P]ATP (Amersham Biosciences K.K.) and T4 polynucleotide kinase (TaKaRa Shuzo Co. Ltd.). An underlined sequence represents PPRE. The binding reaction was performed in 20 µl of a solution including 1 µg of poly (dI-dC), 1 µl of the in vitro synthesized nuclear receptor solution, and 200,000 cpm of the labeled probe. After mixing, it was incubated for 20 minutes at 25° C. and was left for 15 minutes at 4° C. The labeled probe binding to nuclear receptors was separated from the free probe by electrophoresis using 4% of polyacrylamide gel. The electrophoresis was executed using 0.5× TBE buffer (45 mM Tris, 45 mM boric acid, and 1 m M EDTA) for 90 minutes under a voltage of 200V. After the electrophoresis, the gel was dried and analyzed by BAS2500 system (Fuji Photo Film Co., Ltd.). To confirm that the labeled probe binds to nuclear receptors specifically, the competitive reactions were executed. The competitive reactions were executed by adding 10 or 50 times-higher concentration of the unlabeled probe containing wild-type PPRE or mutated PPRE (5'-TGG TTT TGACTTTTGttCCAT CTT C-3' (SEQ ID NO:9), and 5'-GAA GAT GGaaCAAAAGTCAAA ACC A-3' (SEQ ID NO:10)). The mutated nucleotides are represented by small letters. An underlined sequence represents PPRE. FIG. 8 shows the result. The arrow indicates a band of the labeled probe binding to nuclear receptors. When both PPARγ and RXRα existed, the band of the complex was detected (lane 4). When adding an excessive amount of unlabeled oligoDNAs whose PPRE was intact, the band was disappeared in a concentration dependent manner (lane 5 and lane 6). However, when adding unlabeled oligoDNAs with mutated PPRE, the competing effect seen with the wild-type oligoDNAs was attenuated (lane 7 and lane 8). These results revealed that PPARγ/RXR heterodimer specifically binds to the regulatory sequence PPRE identified in human adiponectin promoter region.

EXAMPLE 5

Figure 10:
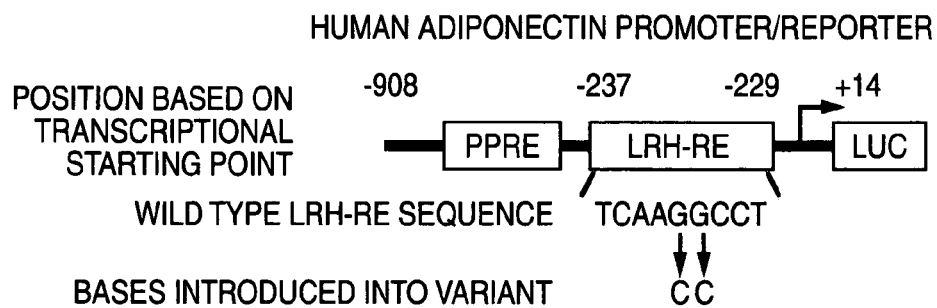
FIG. 10 shows LRH-RE sequence in human adiponectin gene and a structure of human adiponectin promoter/reporter plasmid DNA mutated in LRH-RE sequence.
Figure 11:
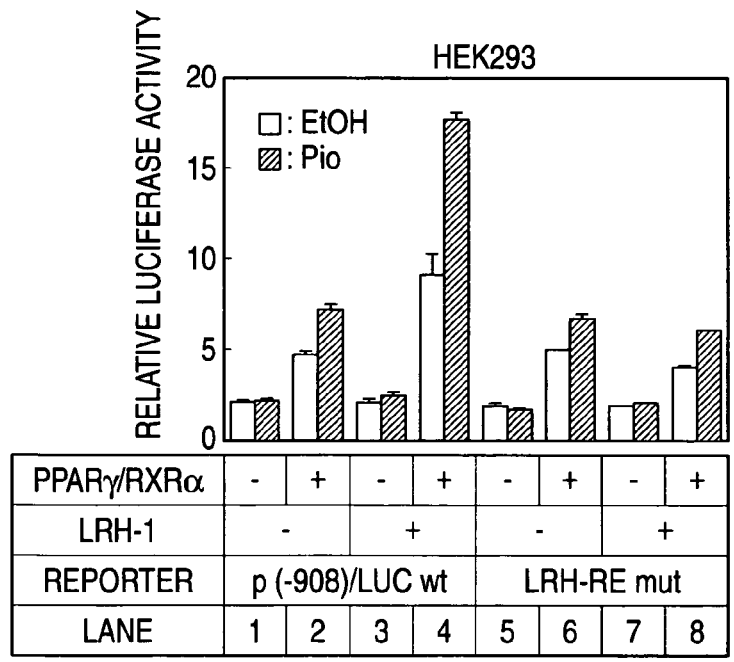
FIG. 11 shows transcriptional activities of human adiponectin promoter/reporter plasmid DNAs enhanced by pioglitazone when PPARγ/RXR heterodimer and/or LRH-1 is/are expressed.

Identification of the Regulatory Sequence (LRH-RE) in Human Adiponectin Promoter Region To clarify whether a regulatory sequences other than PPRE exists in human adiponectin promoter region, the nucleotide sequence of adiponectin promoter was intensively analyzed. As a result, we discovered a sequence presumed to be the regulatory sequence LRH-RE (LRH-1 responsive element) to which another nuclear receptor called LRH-1 (Liver Recepter Homologue-1) can bind. FIG. 9 shows the nucleotide sequence of LRH-RE in gene promoter region that has been reported to be transcriptionally regulated by LRH-1 (*Mol. Cell*, 6, 507-515 (2000), *Proc. Natl. Acad. Sci. U.S.A.*, 96, 6660-6665 (1999), *J. Biol. Chem.*, 276, 24767-24773 (2001), *J Biol. Chem.*, 275, 17793-17799 (2000)). Only one base was different between the LRH-RE sequence found in human adiponectin promoter and the LRH-RE in rat and human CYP7A1 gene promoter. FIG. 10 shows the position of the presumed LRH-RE. The presumed LRH-RE was located from −237 bp to −229 bp of the transcription start site of human adiponectin gene. Because the presumed LRH-RE exists in human adiponectin promoter, it was thought that adiponectin promoter could be transcriptionally regulated by nuclear receptor LRH-1. Then, using the above p(−908)/LUC as a reporter plasmid, the expression plasmids of which PPARγ, RXRα, and LRH-1 can be expressed respectively were transiently expressed in HEK293 cells as previously described in Example 2. Pioglitazone, a PPARγ agonist, was added at 1 µM, 8 hours after transfection. FIG. 11 shows the result. The luciferase activity was doubled by the expression of both PPARγ and RXRα. The activity rose further in the presence of pioglitazone (lane 2). On the other hand, the increase in the luciferase activity was not seen with only LRH-1 expression (lane 3). However, when PPARγ, RXRα, and LRH-1 were expressed simultaneously, the luciferase activity was further doubled compared with that in expressing both PPARγ and RXRα. The effect was also seen in the presence of pioglitazone (Lane 4 compared with lane 2). These results revealed that LRH-1, which doesn't act alone, could augment the human adiponectin promoter activity stimulated by PPARγ/RNR heterodimer. Then, to confirm that the action of LRH-1 depends on the presumed LRH-RE, a 2-bp mutation was introduced into the presumed LRH-RE of the reporter plasmid as shown in FIG. 10. As shown in FIG. 11, the increase by PPARγ and RXRα was not influenced by LRH-RE mutation (Lane 6 compared with lane 2.). On the other hand, the further increase in promoter activity by LRH-1 seen with wild-type reporter (lane 4 compared with lane 2.) was completely disappeared (lane 8 compared with lane 6.). These results revealed that the action of LRH-1 would depend on the presumed LRH-RE in human adiponectin promoter region. And, the presumed LRH-RE was thought to function as a regulatory sequence.

EXAMPLE 6

Direct Binding of LRH-1 to the Regulatory Sequence LRH-RE

Figure 12:
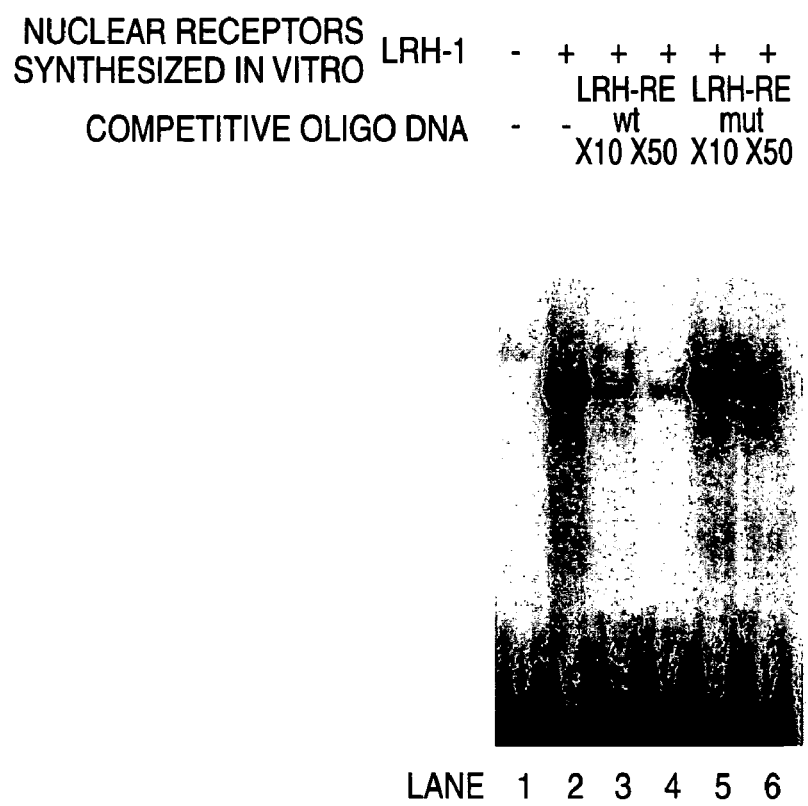
FIG. 12 shows direct binding (gel shift assay) of LRH-1 to the regulatory sequence LRH-RE of human adiponectin promoter.

To confirm the direct binding of LRH-1 to the regulatory sequence LRH-RE found in human adiponectin promoter region, gel shift assay was executed. Gel shift assay was performed as described in Example 4. LRH-1 protein used was synthesized in vitro using human LRH-1 expression plasmid as template. OligoDNAs (5'-AAT AAG GG TCAAGGCCTG GAA ACA C-3' (SEQ ID NO:11) and 5'-GTG TTT CCAGGCCTTGAC CCT TAT T-3' (SEQ ID NO:12)) having a nucleotide sequence from −245 bp to −221 bp in human adiponectin promoter region were used for a labeled probe. An underlined sequence represents LRH-RE. In the competitive reaction, identical oligoDNAs to the labeled probe were used as wild-type competitors. As mutant competitors, oligoDNAs (5'-AAT AAG GGTCAAccCCTG GAA ACA C-3' (SEQ ID NO:13) and 5'-GTG TTT CC AGGggTTGAC CCT TAT T-3'. (SEQ ID NO:14)) mutated as described in FIG. 10 were used. 10 times or 50 times higher concentration of each unlabeled oligoDNAs was added into the reaction. The small letter means a mutated base. The underlined sequence represents LRH-RE. FIG. 12 shows the result. The complex of LRH-1 and the wild-type labeled probe was detected as pointed by an arrow (lane 2). When an excessive amount of wild-type unlabeled oligoDNAs were added, the band was disappeared in a concentration dependent manner (lane 3 and lane 4). On the other hand, when an excessive amount of mutated unlabeled oligoDNAs added, the band of the complex slightly attenuated (lane 5 and lane 6). These results revealed that LRH-1 could specifically bind to the regulatory sequence LRH-RE identified in human adiponectin promoter region.

EXAMPLE 7

Roles of the Identified Regulatory Sequence PPRE and LRH-RE in Adipocytes

Figure 13:
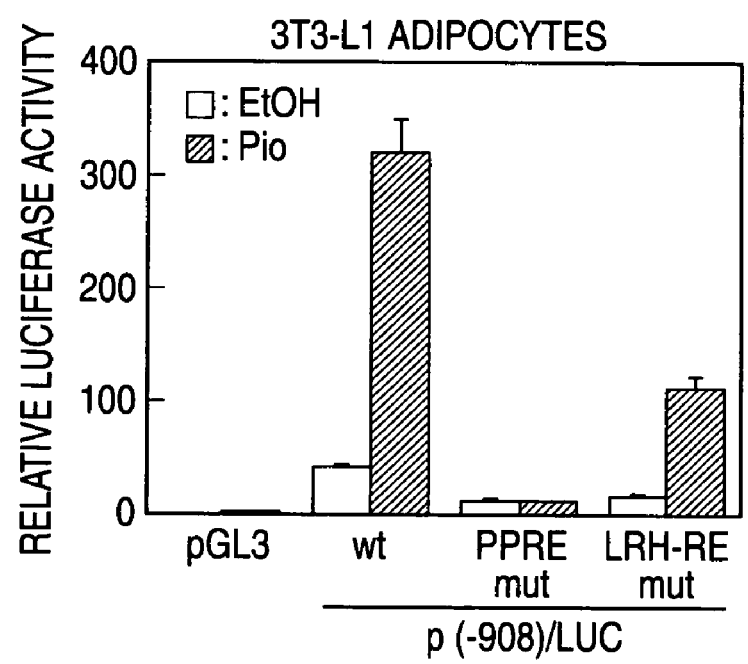
FIG. 13 shows transcriptional activities of the wild-type or mutated human adiponectin promoter/reporter plasmid DNAs enhanced by pioglitazone in differentiated adipocytes.

To indicate whether the identified regulatory sequence PPRE and LRH-RE could take part in transcriptional activation of adiponectin gene in adipocytes, the following experiment was performed. Mouse 3T3-L1 cells were cultured by using 6-well plate (Becton, Dickinson & Company) coated by type IV collagen and the differentiation was induced in medium containing 5 μg/ml of insulin, 0.5 mM isobutylmethylxanthine, and 1 μM dexamethasone. The 6th-day cells from the differentiation induction were used for transformation. LipofectAMINE 2000 reagent (Invitrogen Corporation) was used for transfection according to a supplyer's protocol. 2 μg of reporter plasmid and 1 μg of beta-galactosidase expression plasmid for internal standard per well were used, respectively. The mixture of LipofectAMINE 2000 reagent and plasmids diluted with OPTI-MEM were added to cells, which were incubated for 3.5 hours. Then, the equivalent volume of medium containing 20% of fetal bovine serum was added to the culture. After 44 hours, the luciferase activity and the beta-galactosidase activity were measured. When the medium containing 20% of fetal bovine serum was added, pioglitazone was added at 1 μM. FIG. 13 shows the result. When using wild-type p(−908)/LUC reporter, the luciferase activity was 19-times higher than that of promoter-less pGL3 basic plasmid. In the presence of 1 μM pioglitazone, further increase was seen. It was 9-times higher than without pioglitazone. The luciferase activity of the PPRE-mutated promoter (FIG. 6) remarkably decreased compared with that of the wild-type promoter, and the effect of pioglitazone was not observed at all. When the LRH-RE-mutated promoter (FIG. 10) was used, the luciferase activity also decreased compared with that of the wild-type promoter. However, the luciferase activity of the cells processed by pioglitazone has increased 7.5 times-higher than that without pioglitazone and the response to pioglitazone was remained. These results revealed that the identified regulatory sequence PPRE and LRH-RE played an important role in the activation of adiponectin promoter in adipocytes. Concurrently, it was thought that these regulatory sequences could deeply take part in adiponectin gene expression in a physiological condition.

INDUSTRIAL APPLICABILITY

The nucleotide sequence PPRE (located between 5' upstream 273rd and 285th of the transcription start site in human adiponectin gene) and LRH-RE (located between 5' upstream 229th and 237th as well as the above PPRE) are regulatory sequences in human adiponectin promoter region, and are sequences that nuclear receptor PPARγ, RXR, and LRH-1 bind directly, and play important roles in physiological activation of adiponectin promoter in adipocytes. Transformants transformed with reporter plasmids containing the promoter region with these regulatory sequences and suitable reporter genes approximate the physiological expression pattern of human adiponectin gene, and are extremely useful to screen therapeutic drugs for human diseases.

---

The invention claimed is:

1. A screening method for identifying a compound, or a salt thereof, which enhances human adiponectin promoter activity, comprising the steps of:
   (1) transforming a first and second cell with (a) a DNA molecule comprising the nucleotide sequence of SEQ ID NO:1 operatively linked to a DNA sequence encoding a reporter, (b) an expression plasmid encoding a human PPARγ protein and (c) an expression plasmid encoding a human RXRα protein;
   (2) contacting said first cell with a diluent containing a test compound;
   (3) contacting said second cell with a diluent lacking said test compound;
   (4) comparing the amount of said reporter that is produced by said first cell and said second cell, and wherein when a greater amount of said reporter is produced by said first cell after contacting with said diluent containing said test compound compared to the amount of said reporter produced by said second cell after contacting with said diluent lacking said test compound, said test compound is identified as enhancing human adiponectin promoter activity.

2. The method according to claim 1, wherein said test compound regulates human PPARγ activity.

3. The method according to claim 1, wherein said test compound regulates human RXRα activity.

4. The method according to claim 1, wherein said test compound regulates human LRH-1 activity.

5. The screening method according to claim 1, wherein step (1) further comprises transforming said first and second cell with an expression plasmid encoding a human LRH-1 protein.

* * * * *

SEQUENCE LISTING

```
<160> NUMBER OF SEQ ID NOS: 22

<210> SEQ ID NO 1
<211> LENGTH: 921
<212> TYPE: DNA
<213> ORGANISM: Homo sapiens
<220> FEATURE:
<221> NAME/KEY: 5'UTR
<222> LOCATION: (1)..(921)

<400> SEQUENCE: 1
cttctaggcc agagctgggt tccacaagag acagaatagg catatatatg cttaaggaac      60
tggaaaaaca ggctctctct ctctcacaaa cacacacaca cataccaa ggtagctgtc       120 aaaatgttat ccgaaatttt ggaaccaaaa aatcttgaaa gatggtattc caatatcaca    180 tttatgtaa gttttctatt atattagatt caaattacga ttcgaggcca caagctttaa     240
gaattcaggg cctttttaac ttgccaagcc ccacaccact ccaggaactt ccccacaccc    300
cagttctcag aattcatgtg caaggtcttt cctaaatcca gggtccaggt cagagagtgg    360
aggatgtgct ctatttctta cctgattgca gacccctctg acagtgctcc cttctgaagc    420
actcactgtc tgaacgtaca cagtctcaga cttaatcatg cacagtgagc aagactgtgg    480
tgtgataatt ggcgtccctg acttattagg gcaaatctat gggaggggga gacctcctgg   540
accactgagc aattaattca tttacattag gaagtttctc cgtcagatgc aggaaaaaaa    600
tcttgttttc ctgctgtggt tttgactttt gccccatctt ctgttgctgt tgtaggaggc    660
```

```
aaaataaggg tcaaggcctg gaaacacaag tgctttgact gaagctccac ttggcttccg      720
aagcccaagc tgggttgtac caggttccct agggtgcagg ctgtgggcaa ctgccaggga      780
catgtgcctg cccaccggcc tctggccctc actgagttgg ccaatgggaa atgacaattg      840
tgaggtgggg actgcctgcc cccgtgagta ccaggctgtt gaggctgggc catctcctcc      900
tcacttccat tctgactgca g                                                921

<210> SEQ ID NO 2
<211> LENGTH: 13
<212> TYPE: DNA
<213> ORGANISM: Homo sapiens

<400> SEQUENCE: 2
tgacttttgc ccc                                                          13

<210> SEQ ID NO 3
<211> LENGTH: 9
<212> TYPE: DNA
<213> ORGANISM: Homo sapiens

<400> SEQUENCE: 3 tcaaggcct                                                                9

<210> SEQ ID NO 4
<211> LENGTH: 57
<212> TYPE: DNA
<213> ORGANISM: Homo sapiens

<400> SEQUENCE: 4
tgacttttgc cccatcttct gttgctgttg taggaggcaa ataagggtc aaggcct          57

<210> SEQ ID NO 5
<211> LENGTH: 35
<212> TYPE: DNA
<213> ORGANISM: Artificial Sequence
<220> FEATURE:
<223> OTHER INFORMATION: PCR primer 1

<400> SEQUENCE: 5
tttcggggta ccgcttctag gccagagctg ggttc                                  35

<210> SEQ ID NO 6
<211> LENGTH: 36
<212> TYPE: DNA
<213> ORGANISM: Artificial Sequence
<220> FEATURE:
<223> OTHER INFORMATION: PCR primer 2

<400> SEQUENCE: 6
tttcgggagc tcctgcagtc agaatggaag tgagaa                                 36

<210> SEQ ID NO 7
<211> LENGTH: 25
<212> TYPE: DNA
<213> ORGANISM: Homo sapiens

<400> SEQUENCE: 7
tggttttgac ttttgcccca tcttc                                             25

<210> SEQ ID NO 8
<211> LENGTH: 25
<212> TYPE: DNA
<213> ORGANISM: Homo sapiens
```

-continued

```
<400> SEQUENCE: 8
gaagatgggg caaaagtcaa aacca                                    25

<210> SEQ ID NO 9
<211> LENGTH: 25
<212> TYPE: DNA
<213> ORGANISM: Artificial Sequence
<220> FEATURE:
<223> OTHER INFORMATION: probe competitor - oligo mutant dna1

<400> SEQUENCE: 9
tggttttgac ttttgttcca tcttc                                    25

<210> SEQ ID NO 10
<211> LENGTH: 25
<212> TYPE: DNA
<213> ORGANISM: Artificial Sequence
<220> FEATURE:
<223> OTHER INFORMATION: probe competitor - oligo mutant dna2

<400> SEQUENCE: 10
gaagatggaa caaaagtcaa aacca                                    25

<210> SEQ ID NO 11
<211> LENGTH: 25
<212> TYPE: DNA
<213> ORGANISM: Homo sapiens

<400> SEQUENCE: 11
aataagggtc aaggcctgga aacac                                    25

<210> SEQ ID NO 12
<211> LENGTH: 25
<212> TYPE: DNA
<213> ORGANISM: Homo sapiens

<400> SEQUENCE: 12
gtgtttccag gccttgaccc ttatt                                    25

<210> SEQ ID NO 13
<211> LENGTH: 25
<212> TYPE: DNA
<213> ORGANISM: Artificial Sequence
<220> FEATURE:
<223> OTHER INFORMATION: probe competitor - oligo mutant dna3

<400> SEQUENCE: 13
aataagggtc aacccctgga aacac                                    25

<210> SEQ ID NO 14
<211> LENGTH: 25
<212> TYPE: DNA
<213> ORGANISM: Artificial Sequence
<220> FEATURE:
<223> OTHER INFORMATION: probe competitor - oligo mutant dna4

<400> SEQUENCE: 14
gtgtttccag gggttgaccc ttatt                                    25

<210> SEQ ID NO 15
<211> LENGTH: 13
<212> TYPE: DNA
<213> ORGANISM: Artificial Sequence
<220> FEATURE:
```

```
<223> OTHER INFORMATION: consensus regulatory sequence PPRE
<220> FEATURE:
<221> NAME/KEY: misc_feature
<222> LOCATION: (7)..(7)
<223> OTHER INFORMATION: n is a, c, g, or t

<400> SEQUENCE: 15
aggtcanagg tca                                                            13

<210> SEQ ID NO 16
<211> LENGTH: 13
<212> TYPE: DNA
<213> ORGANISM: Homo sapiens

<400> SEQUENCE: 16
ggggcaaaag tca                                                            13

<210> SEQ ID NO 17
<211> LENGTH: 13
<212> TYPE: DNA
<213> ORGANISM: Mus sp.

<400> SEQUENCE: 17
gggtgaaatg tgc                                                            13

<210> SEQ ID NO 18
<211> LENGTH: 13
<212> TYPE: DNA
<213> ORGANISM: Mus sp.

<400> SEQUENCE: 18
ggatcagagt tca                                                            13

<210> SEQ ID NO 19
<211> LENGTH: 13
<212> TYPE: DNA
<213> ORGANISM: Mus sp.

<400> SEQUENCE: 19
aggctaaagg tca                                                            13

<210> SEQ ID NO 20
<211> LENGTH: 13
<212> TYPE: DNA
<213> ORGANISM: Mus sp.

<400> SEQUENCE: 20
ggggcaaagt tca                                                            13

<210> SEQ ID NO 21
<211> LENGTH: 13
<212> TYPE: DNA
<213> ORGANISM: Mus sp.

<400> SEQUENCE: 21
aggggagagg tca                                                            13

<210> SEQ ID NO 22
<211> LENGTH: 13
```

```
<212> TYPE: DNA
<213> ORGANISM: Homo sapiens

<400> SEQUENCE: 22
actgaaaacg ggg                                                    13
```